United States Patent
Bei et al.

(10) Patent No.: US 6,339,157 B1
(45) Date of Patent: Jan. 15, 2002

(54) SYNTHESIS OF CARBOXAMIDES FROM THE CATALYZED REACTION OF ALDEHYDES AND AMINES

(75) Inventors: Xiaohong Bei, Santa Clara; Anil Guram, San Jose, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/627,736

(22) Filed: Jul. 28, 2000

Related U.S. Application Data

(63) Continuation-in-part of application No. 09/531,855, filed on Mar. 21, 2000, which is a continuation-in-part of application No. 09/378,107, filed on Aug. 20, 1999, now Pat. No. 6,268,513, which is a continuation-in-part of application No. 09/296,226, filed on Apr. 22, 1999, now Pat. No. 6,265,601.
(60) Provisional application No. 60/095,612, filed on Aug. 6, 1998.

(51) Int. Cl.$^7$ .................. C07D 295/00; C07C 231/10; C07F 9/02
(52) U.S. Cl. .................. 544/386; 544/391; 556/21; 564/182; 564/183; 564/184; 564/185
(58) Field of Search .................. 564/185, 184, 564/183, 182; 544/386, 391; 556/21

(56) References Cited

U.S. PATENT DOCUMENTS

| | | | | |
|---|---|---|---|---|
| 1,564,631 A | * | 12/1925 | Schmidt | 564/185 |
| 3,024,282 A | * | 3/1962 | Parris | 260/562 |
| 4,346,101 A | * | 8/1982 | Lednicer | 424/278 |
| 4,933,493 A | * | 6/1990 | Martin et al. | 564/185 |
| 6,265,601 B1 | * | 7/2001 | Guram et al. | 558/411 |
| 6,268,513 B1 | * | 7/2001 | Guram et al. | 549/200 |

OTHER PUBLICATIONS

Beller et al., *Angew. Chem. Int. Ed.*, 2000, 39, 1010–1027.
Boche, et al., *Tetrahedron Lett.*1982, 23, 3255.
Hassner et al. Tetrahedron Organic Chemistry Series vol. 11: Organic Syntheses Based On Named and Unnamed Reactions, Pergamon 1994, p. 4.
Hassner et al. Tetrahedron Organic Chemistry Series vol. 11: Organic Syntheses Based On Named and Unnamed Reactions, Pergamon 1994, p. 289.
Goetz, H., et al., *Liebigs Ann. Chem.*(1977), No. 4, pp. 556–564.

* cited by examiner

*Primary Examiner*—Porfirio Nazario-Gonzalez

(57) ABSTRACT

Aldehydes are catalytically combined with amines to form carboxamides in one step using an oxidant and a metal-ligand complex or metal/ligand composition.

17 Claims, No Drawings

SYNTHESIS OF CARBOXAMIDES FROM THE CATALYZED REACTION OF ALDEHYDES AND AMINES

BENEFIT CLAIM

This application is a continuation-in-part of U.S. patent application Ser. No. 09/531,855, filed Mar. 21, 2000 which is a continuation-in-part of U.S. patent application Ser. No. 09/378,107, filed Aug. 20, 1999, now U.S. Pat. No. 6,268,513 B1, which is a continuation-in-part of U.S. patent application Ser. No. 09/296,226, filed Apr. 22, 1999, now U.S. Pat. No. 6,265,601 B1, which claims the benefit of U.S. Provisional Application No. 60/095,612, filed Aug. 6, 1998. The disclosures of all of these applications are incorporated herein by reference.

FIELD OF THE INVENTION

The present invention relates to a process for the synthesis of amides from the reaction of an aldehyde with a primary or secondary amine in the presence of a catalyst and suitable additives and solvents. The catalyst is a metal complex, which may be in the form of a metal-ligand complex or metal precursor/ligand composition.

BACKGROUND OF THE INVENTION

Carboxamides represent important synthetic intermediates for a variety of applications in pharmaceutical, chemical, and polymer industries. Generally, carboxamides are molecules that have a covalent bond between a carboxyl carbon and a nitrogen atom, i.e., C(O)—N.

Carboxamides are known to be synthesized from the reactions of acids, acid halides and esters with amines. The synthesis of carboxamides from the reaction of aryl halides or alkyl halides or alkenes with carbon monoxides and amines (amidocarbonylation) is also known in the art. Many different process conditions and catalysts have been developed for these transformations. These reactions however, do not use readily available aldehydes.

In contrast, methods for carboxamide synthesis from aldehydes are fairly limited. One carbon higher homologous amides can be synthesized from the reaction of aldehydes with carbon monoxide and amines (amidocarbonylation; see, e.g., Beller et al., *Angew. Chem. Int. Ed.*, 2000, 39, 1010–1027, incorporated herein by reference, for a recent review) in presence of suitable catalysts. Carboxamides can also be synthesized from aldehydes in a multiple step (4 step) synthetic sequence (Boche, et al., *Tetrahedron Lett.* 1982, 23, 3255), but this process involves industrially undesirable reagents and process conditions. Other highly specific methods for the synthesis of specific carboxamides from the reaction of specific aldehydes and amines include the Angelini-Rimini synthesis of hydroxamic acids from the reaction of aidehydes and N-sulfonylhydroxylamine (Hassner et al. Tetrahedron Organic Chemistry Series Volume 11: Organic Syntheses Based On Named and Unnamed Reactions, Pergamon 1994, p. 4), and the is Passerini synthesis of α-hydroxycarboxamides from the reaction of an aldehyde or ketone with an isocyanide (Hassner et al., Id., p. 289). These methods are of limited scope and are not applicable for the general direct synthesis of carboxamides from aldehydes.

Thus, given the ready availability of aldehydes, it is desirable to have an industrially viable, general, and direct method for the synthesis of carboxamides from the reaction of aldehydes and amines.

SUMMARY OF THE INVENTION

This invention provides a new method for the synthesis of carboxamides from the metal precursor complex—ligand composition catalyzed reaction of aldehydes and amines, and alleviates many of the problems associated with the current methods for the synthesis of carboxamides from aldehydes. This invention offers the benefit of direct and economical conversion of aldehyde to carboxamides. This invention offers the additional benefit of higher functional group compatibility. The method utilizes industrially viable reagents and solvents.

The present invention offers a process for the synthesis of carboxamides by reacting a mixture of an aldehyde, an amine, an oxidant and a base in the presence of metal-ligand complex or composition as a catalyst and a suitable solvent. The products are the result of the formation of the carbon-nitrogen bond from the amine/aldehyde combination. The invention identifies process conditions, which surprisingly result in the selective and predominant formation of the carboxamide rather than aryl amines resulting from the reaction of amines with halobenzene (oxidant).

In another embodiment, this invention provides for the synthesis of carboxamides from an alcohol and an amine. The reaction proceeds by oxidizing the alcohol to the corresponding aldehyde and subsequent reaction of the aldehyde product with an amine to form the carboxamide. The embodiment can proceed as a one-pot synthesis with sequential or substantially concurrent (e.g., simultaneous) addition of reactants and catalyst.

Thus, it is an object of this invention to provide a process for the formation of a carboxamide from the reaction of an amine and an aldehyde.

It is another object of this invention to provide a process for the formation of a carboxamide from the metal precursor complex—ligand catalyzed reaction of an amine and an aldehyde.

It is a further object of this invention to provide a process for the formation of a carboxamide from the reaction of an amine and an aldehyde where the amine and/or aldehyde comprises other reactive functionalities.

It is yet a further object of this invention to form a carboxamide from the reaction of an amine and an aldehyde under mild, and economically and/or environmentally sound conditions.

It is still a further object of this invention to form a carboxamide in a one-pot synthesis reaction starting from an alcohol substrate and an amine.

These and other objects of the invention are accomplished through a reaction using suitable metal-ligand compositions or complexes that can be generated in situ or separately by adding suitable ligands to suitable precursor metals. Suitable ligands of this process can be characterized by the general formulas $PR_3$, $NR_3$, $SR_2$, $OR_2$, or $:CR_2$ (carbenes) wherein each R is independently selected from the group consisting of hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.). Suitable precursor metal complexes can be characterized by the form $ML_n$ wherein M is a transition metal, preferably Pd, Ni, Ru, Rh, Co, Ir, and most preferably Pd and Ni and L is a suitable neutral or charged organic or inorganic fragment or solid support. Suitable bases of this process can be organic and inorganic compounds such as amines, alkali and alkaline earth metal carbonates, phosphates, alkoxides, hydroxides and fluorides. Suitable solvents include hydrocarbons, ethers, ketones, alcohols, and nitriles.

Further aspects of this invention will be evident to those of skill in the art upon review of this specification.

DETAILED DESCRIPTION OF THE INVENTION

It is to be understood that unless otherwise indicated this invention is not limited to specific reactants, catalyst compositions (including heteroatom-containing activators and acids), or synthetic methods. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, reference to "a reagent" includes mixtures of reagents, "a base" includes mixtures of bases, "a catalyst composition" includes mixtures of catalyst compositions, and the like.

In describing and claiming the present invention, the following terminology will be used in accordance with the definitions set out below. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The following definitions pertain to chemical structures, molecular segments and substituents:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different (e.g., $R^2$ and $R^3$ in the structure of formula (II) may all be substituted alkyl groups, or $R^2$ may be hydrido and $R^3$ may be methyl, etc.).

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms. The term "aryloxy" is used in a similar fashion, with aryl as defined below.

Similarly, the term "alkyl thio" as used herein intends an alkyl group bound through a single, terminal thioether linkage; that is, an "alkyl thio" group may be represented as -S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH=C'CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. The term "hydrocarbyline" intends a trivalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. Thus, a "hydrocarbyline" may include a "hydrocarbylene." "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

As used herein the term "silyl" refers to the $-SiZ^1Z^2Z^3$ radical, where each of $Z^1$, $Z^2$, and $Z^3$ is independently selected from the group consisting of hydrido and optionally substituted alkyl, alkenyl, alkynyl, aryl, aralkyl, alkaryl, heterocyclic, alkoxy, aryloxy and amino.

As used herein, the term "phosphino" refers to the group $-PZ^1Z^2$, where each of $Z^1$ and $Z^2$ is independently selected from the group consisting of hydrido and optionally substituted alkyl, alkenyl, alkynyl, aryl, aralkyl, alkaryl, heterocyclic and amino.

The term "amino" is used herein to refer to the group $-NZ^1Z^2$, where each of $Z^1$ and $Z^2$ is independently selected from the group consisting of hydrido and optionally substituted alkyl, alkenyl, alkynyl, aryl, aralkyl, alkaryl and heterocyclic.

The term "thio" is used herein to refer to the group $-SZ^1$, where $Z^1$ is selected from the group consisting of hydrido and optionally substituted alkyl, alkenyl, alkynyl, aryl, aralkyl, alkaryl and heterocyclic.

The term "substrate" refers generally to a reactant, e.g., the "aldehyde" or "amine" herein. Additional abbreviations used herein include "Cy" to refer to a cyclohexyl group (and thus, "$Cy_2$" refers to two cyclohexyl groups, etc.).

As used herein all reference to the elements and groups of the Periodic Table of the Elements is to the version of the table published by the Handbook of Chemistry and Physics, CRC Press, 1995, which sets forth the new IUPAC system for numbering groups.

In one embodiment, then, the reaction of this invention is believed to proceed by Scheme 1, shown below:

Scheme 1

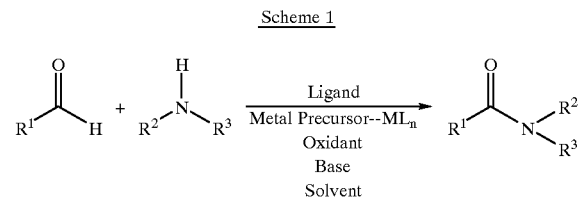

Substrates

The starting aldehyde substrate for the process, as shown in Scheme 1, may be characterized by the general formula (I): $R^1CHO$, where $R^1$ is selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.). In more preferred embodiments, $R^1$ is selected from the group consisting of alkyl, substituted alkyl, heteroatom-containing alkyl, substituted heteroatom-containing alkyl, aryl, substituted aryl, heteroatom-containing aryl and substituted heteroatom-containing aryl. Specific embodiments within the scope of formula I, include:

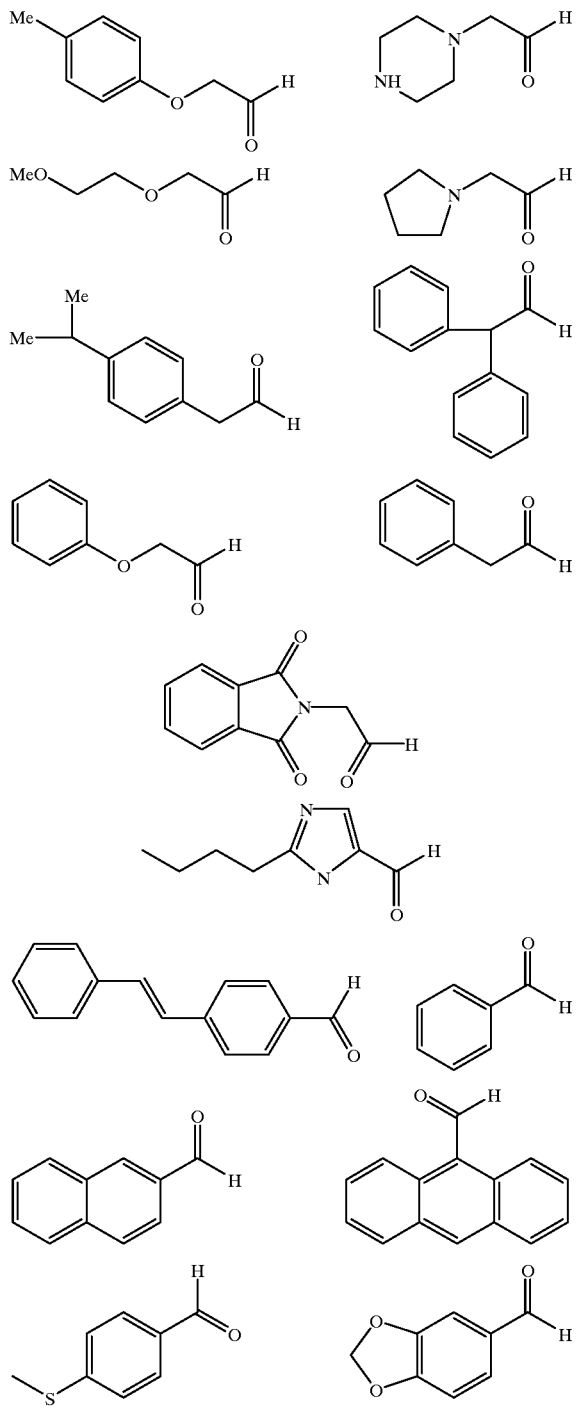

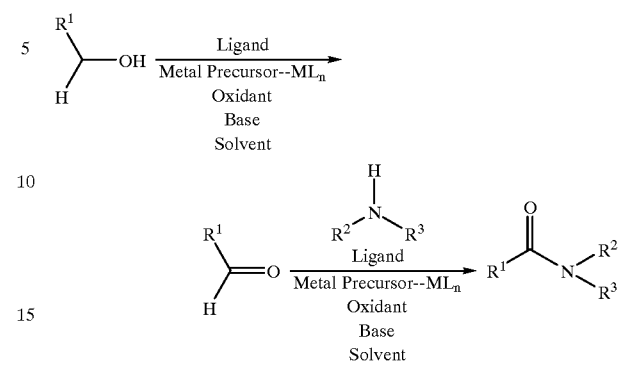

Scheme 2

Since the conditions and catalytic materials are similar if not identical, this reaction proceeds smoothly. Starting alcohol substrates have the same definition of $R^1$ as discussed above. $R^1$, $R^2$ and $R^3$ have the same meanings used herein.

The starting amine is either a primary or secondary amine as shown above in scheme 1 and may be characterized by the general formula (II): $R^2R^3NH$, where each of $R^2$ and $R^3$ is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl alkenyl, alkynyl, aryl, aralkyl, alkaryl, etc.). In addition, either $R^2$ or $R^3$ may be hydrogen, but both cannot be hydrogen at the same time. In more specific embodiments, $R^2$ and $R^3$ are each independently selected from the group consisting of alkyl, substituted alkyl, heteroatom-containing alkyl, substituted heteroatom-containing alkyl, aryl, substituted aryl, heteroatom-containing aryl, substituted heteroatom-containing aryl, aralkyl, substituted aralkyl, heteroatom containing aralkyl and substituted heteroatom containing aralkyl. In other embodiments, $R^2$ and $R^3$ are joined together in a ring structure, where the ring backbone (N, $R^2$ and $R^3$) has from 3 to 50 non-hydrogen atoms, including bicyclic or other multi-cyclic ring structures as are known in the art. In some preferred embodiments, the ring backbone additionally contains one or more heteroatoms in the $R^2$ or $R^3$ definition. Examples of ring structures include, but are not limited to, pyrrolidines (including substituted pyrrolidine, heteroatom-containing pyrrolidine and substituted heteroatom containing pyrrolidine), piperidines (including substituted piperidine, heteroatom-containing piperidine and substituted heteroatom containing piperidine), morpholines (including substituted morpholine, heteroatom-containing morpholine and substituted heteroatom containing morpholine) and the like. Specific examples of amines include:

In another embodiment, the starting aldehyde substrate is generated in a synthesis reaction from a starting alcohol substrate that is oxidized to the aldehyde. This type of reaction is disclosed and described is commonly owned and co-pending U.S. patent application Ser. No. 09/531,855, filed Mar. 21, 2000, which is incorporated herein by reference. The aldehyde can be generated and used without being isolated, in a one-pot scheme that may generally be described by below Scheme 2:

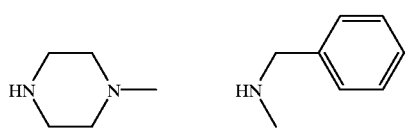

Oxidants

The oxidants useful in this invention may be any suitable aryl halide, which may be characterized by the general formula:

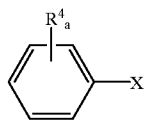
(III)

where $R^4$ is selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, and combinations thereof; a is 0, 1, 2, 3, 4 or 5; and X is Cl, Br, F or I. Optionally two or more $R^4$ groups are joined together in a ring structure. Preferable, $R^4$ is selected from the group consisting of hydrogen, methyl, ethyl, tert-butyl, methoxy, —CN and —CF$_3$. Also, preferably, a is 0, 1, 2 or 3. The most preferred oxidant is chlorobenzene.

Ligands

The ligands useful in this invention can be characterized by the general formula PR$_3$, where each R is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.). Other ligands that are useful in this invention include carbenes that can be characterized by the formula :CR$_2$, where each R is as defined above. Also useful in this invention are ligands such as NR$_3$ and OR$_2$ where each R is as defined above. In preferred embodiments, one or more R groups in the above formulas is independently selected from the group consisting of alkyl and substituted alkyl, with cycloalkyl and substituted cycloalkyl being preferred for at least one R group. Generally, all of the above-defined ligands are useful, with the phosphines being particularly preferred.

In a more particular embodiment, preferred ligands useful in this invention are mono-phosphine ligands that are characterized by the general formula:

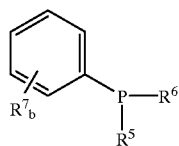
(IV)

wherein each $R^5$ and $R^6$ is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.); and $R^7$ is selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, and combinations thereof, and b is 0, 1, 2, 3, 4 or 5. Optionally two or more $R^7$ groups are joined together in a ring structure. Specific preferred embodiments of $R^7$ are alkyl, substituted alkyl, aryl, substituted aryl, heteroatom-containing alkyl, substituted heteroatom-containing alkyl, heteroatom-containing aryl, and substituted heteroatom-containing aryl.

In an alternative embodiment, the phosphine ligands useful in this invention have a cyclopentadienyl ring, and may be characterized by the formula:

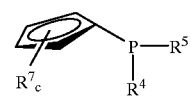
(V)

where $R^4$ and $R^5$ are defined as above and each $R^7$ is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, nitro, ester, acid, alkoxy, aryloxy, hydroxy, metallocene, transition metals, COOH, SO$_3$G (G=Na, K, H, etc.) and combinations thereof; c is 0, 1, 2, 3 or 4 and $R^7$ can occupy any available site on the cyclopentadienyl ring, including an eta-bond (such as an $\eta^5$ bond). More specific embodiments of $R^7$ are those where a mono-cyclopentadienyl or bis-cyclopentadienyl metallocene is formed as part of the ligand. Thus, $R^7$ may be a moiety having a metal atom selected from the group consisting of metals from the Periodic Table of Elements, such as Fe, Rh, Mo, Ru, Cr, Zr, Ti, Hf. Co. Specific examples of $R^7$ include FeCp, CrCp and ZrCpR$_2$, where Cp is a substituted or unsubstituted cyclopentadienyl and R is as defined above. In this specific embodiment, it is intended that the bond between the Cp ring in the ligand and $R^7$ is an $\eta^5$ bond.

Specific embodiments of preferred ligand include:

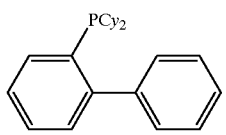 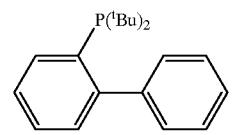

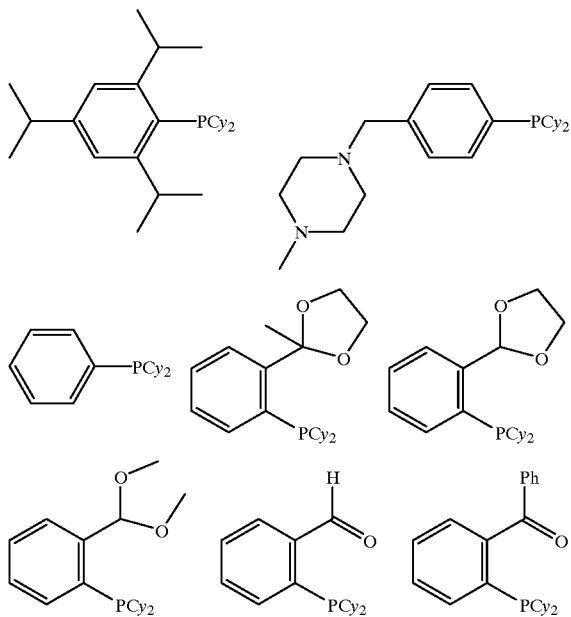

The ligands useful in this invention may be on a support or not. For example, the support could be attached to any one of the R groups. In that embodiment, the support may be a polymer or functionalized polymer, such as polystyrene. In the case of heterogeneous reactions, the ligands may be supported, with or without the metal coordinated (discussed below), on an organic or inorganic support. Suitable supports include silicas, aluminas, zeolites, polyethyleneglycols, polystyrenes, polyesters, polyamides, peptides and the like.

Generally, the ligands useful in this invention may be purchased or prepared using methods known to those of skill in the art. Specific synthesis methods are shown in U.S. patent application Ser. No. 09/062,128, filed Apr. 17, 1998; U.S. patent application Ser. No. 09/296,226, filed Apr. 22, 1999; and U.S. patent application Ser. No. 09/252,182, filed Feb. 18, 1999, each of which are incorporated herein by reference for all purposes. See also, for example, Goetz, H., et al., *Liebigs Ann. Chem.* (1977), No. 4, pp. 556–564.

Metals

The ligand is combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ (also referred to as $ML_n$ or $M-L_n$) where M is a metal selected from the group consisting of Groups 5, 6, 7, 8, 9 and 10 of the Periodic Table of Elements. In more specific embodiments, M is selected from the group consisting of Ni, Pd, Fe, Pt, Ru, Rh, Ir and Co. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, alkoxy, aryloxy, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, amino, and combinations thereof. Specific examples of suitable metal precursor compounds include $Pd(dba)_2$ (where dba=dibenzylydieneacteone), $Pd_2(dba)_3$, $Pd(OAc)_2$ (where Ac=acetate), $PdCl_2$, $Pd(TFA)_2$ (where TFA=trifluoroacetate) and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be a L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

Solvents

Solvents suitable for the process of the invention are, for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), certain alcohols (e.g., tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dioxane, THF), hydrocarbons (e.g., cyclohexane, benzene, toluene, xylene), water and combinations thereof. Most particularly preferred are benzene, toluene, xylene, dioxane, THF, water and combinations thereof.

Bases

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, tertiary amines, alkali metal and alkaline earth fluorides, and ammonium fluorides. Particularly preferred are alkali metal and alkaline earth metal phosphates, alkali metal and alkaline earth metal carbonates, alkali metal hydrogen carbonates, alkali metal and alkaline earth fluorides. Most particularly preferred are alkali metal phosphates, alkali metal and alkaline earth metal carbonates, alkali metal and alkaline earth metal alkoxides, and alkali metal and alkaline earth metal hydroxides (such as potassium phosphate and potassium carbonate). Also, specific bases are discussed in the examples, but could also include NaO$^t$Bu. The base is preferably used in the process of the invention in an amount of from about 1 to about 1000 mol %, particularly preferably from about 50 to about 500 mol %, very particularly preferably from about 100 to about 400 mol %, in particular from about 150 to about 300 mol %, based on the starting amine substrate.

Processes

The process of this invention is accomplished by following the reaction outlined generally in Scheme 1, above.

The metal portion of the catalyst (metal precursor or metal complex) is used in the process of this invention in a proportion of from about 0.000001 to about 10 mol %, preferably from about 0.01 to about 5 mol %, particularly preferably from about 0.5 to about 3 mol %, most particularly preferably from about 1.0 to about 1.2 mol %, based on the starting amine substrate. The ligand is used in the process in a proportion of from about 0.0000001 to about 40 mol %, preferably from about 0.03 to about 1 mol %, particularly preferably from about 1.5 to about 10 mol %, most particularly preferably from about 1 to about 6 mol %, based on the starting amine substrate.

To carry out the process of this invention, the aldehyde substrate, amino substrate, oxidant, base, a catalytic amount of metal precursor and a catalytic amount of the ligand are added to an inert solvent or inert solvent mixture. In a batch methodology, this mixture is stirred at a temperature of from 0° C. to 200° C., preferably at from 30° C. to 170° C., particularly preferably at from 50° C. to 150° C., most particularly preferably at from 60° C. to 120° C., for a period of 5 minutes to 100 hours, preferably from 15 minutes to 70 hours, particularly preferably from ½ hour to 50 hours, most particularly preferably from 1 hour to 30 hours. The crude product is freed of the solvent or the solvents and is subsequently purified by methods known to those skilled in the art and matched to the respective product, e.g. by recrystallization, distillation, sublimation, zone melting, melt crystallization or chromatography.

Without wishing to be bound by any particular theory or mechanism, it is believed that the below mechanism is relevant, as shown in the following Scheme 3:

Scheme 3

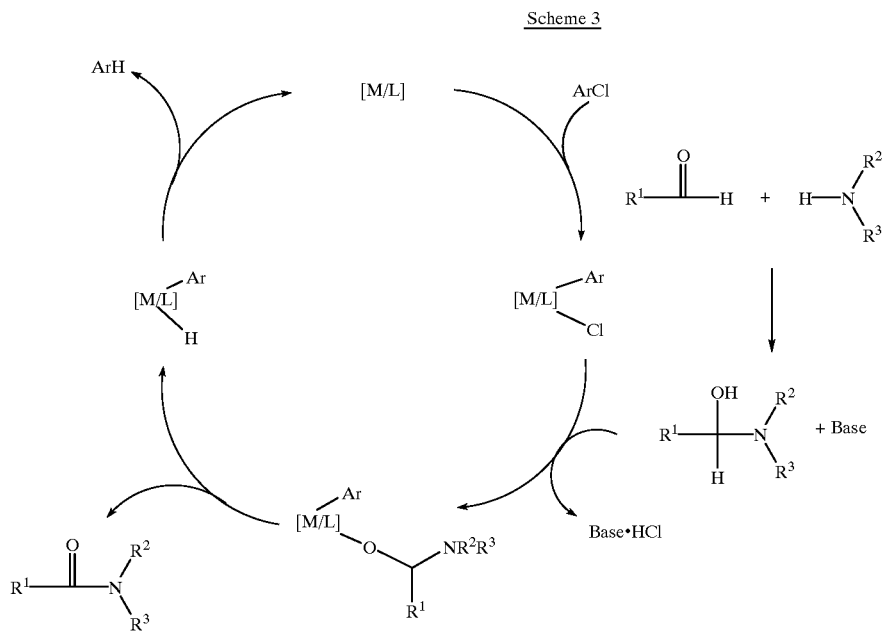

All of the starting materials are added to the processes at one time. Also in Scheme 3, M/L is used to represent the metal/ligand composition or complex (e.g., not the metal precursor only); "Ar" refers to the aryl portion of an aryl chloride oxidant (which is the example used in Scheme 3 although other aryl halide oxidants are useful). More specifically discussing Scheme 3, it is proposed that the ligand/ metal composition or complex begins at the top, shown with [M/L] to indicate the composition or complex as discussed above. It is further proposed that the exemplified aryl chloride oxidatively adds forming a complex that reacts with the starting aldehyde and amine substrates, which, essentially, have been deprotonated by the base. It is proposed that by beta hydride elimination, the product amide is dissociated from the metal. The reduced aryl chloride (e.g., benzene or benzene derivative) also dissociates from the metal/ligand composition or complex. Thus, those of skill in the art will appreciate that the metal (e.g., metal precursor), ligand, aryl chloride and aldehyde and amine substrates may be chosen to avoid side product or undesired product formation.

Products of the process of the invention are carboxamides. These products are suitable as precursors or intermediates for pharmaceuticals and polymers, including additives for the same. The other product is the halide-abstracted aryl halide oxidant that may act like a solvent, which is typically separated from the carboxamide product by techniques known to those of skill in the art for the removal of solvents (such as distillation, evaporation, etc.).

EXAMPLES

General:

All reactions were performed under argon atmosphere in oven-dried glass Schlenk tubes using standard Schlenk techniques. All aldehydes, amines, bases ($Na_2CO_3$, $K_2CO_3$, $K_3PO_4$), chlorobenzene (PhCl), bis(dibenzylideneacetone) palladium (a.k.a., $Pd(dba)_2$), palladium(II) acetate (a.k.a., $Pd(OAc)_2$, diethyl ether, toluene were purchased from commercial sources and used as received. All solvents were of the anhydrous, sure-seal grade. All reactions were performed until complete consumption of the starting amine substrate, unless indicated otherwise; but the reaction times and conditions have not been minimized. Ligand A has the structure

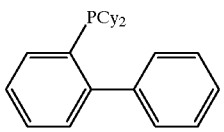

and can be purchased from Strem Chemical.

The following reaction schemes were followed in the examples, generally:

Examples 1–2:

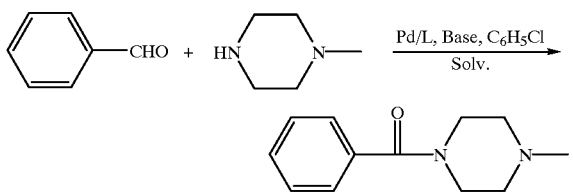

Examples 3–5:

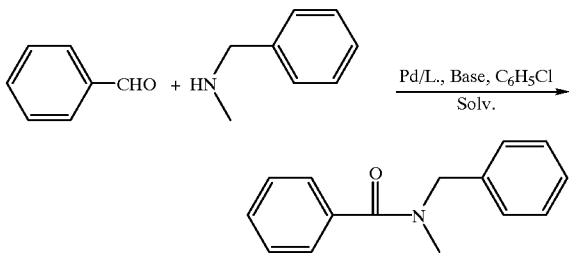

Example 1:

A Schlenk tube containing a mixture of $K_3PO_4$ (420 mg, 1.98 mmol), $Pd(dba)_2$ (11 mg, 19 μmol), Ligand A (20 mg, 57 μmol) was degassed thoroughly under vacuum and refilled with argon. Benzaldehyde (0.20 mL, 1.97 mmol), 1-methylpiperazine (0.11 mL, 0.99 mmol), chlorobenzene (0.15 mL, 1.47 mmol) and toluene (3 mL) were added. The mixture was heated to 105° C. for 21.5 h. GC-MS analysis indicated complete conversion of 1-methylpiperazine. The desired carboxamide product was formed in 86% yield.

Example 2:

A Schlenk tube containing a mixture of $Na_2CO_3$ (210 mg, 1.98 mmol), $Pd(dba)_2$ (11 mg, 19 μmol), Ligand A (20 mg, 57 μmol) was degassed thoroughly under vacuum and refilled with argon. Benzaldehyde (0.20 mL, 1.97 mmol), 1-methylpiperazine (0.11 mL, 0.99 mmol), chlorobenzene (0.15 mL, 1.47 mmol) and toluene/$H_2O$ (3/1 mL) were added to the schlenk. The mixture was heated to 95–100° C. for 24 h. GC-MS analysis indicated 87% conversion of 1-methylpiperazine. The desired carboxamide product was formed in 80% yield.

Example 3:

A Schlenk tube containing a mixture of $K_3PO_4$ (424 mg, 2.0 mmol), $Pd(OAc)_2$ (5 mg, 22 μmol), Ligand A (22 mg, 63 μmol) was degassed thoroughly under vacuum and refilled with argon. Benzaldehyde (0.20 mL, 1.97 mmol), N,N-methylbenzylamine (0.12 mL, 0.99 mmol), chlorobenzene (0.15 mL, 1.47 mmol) and toluene (3 mL) were added to the schlenk. The mixture was heated to 105° C. for 24 h. GC-MS analysis indicated complete conversion of N-methylbenzylamine. The desired carboxamide product was formed in 72% yield.

Example 4:

A Schlenk tube containing a mixture of $K_3PO_4$ (424 mg, 2.0 mmol), $Pd(dba)_2$ (6 mg, 10 μmol), Ligand A (11 mg, 31 μmol) was degassed thoroughly under vacuum and refilled with argon. Benzaldehyde (0.20 mL, 1.97 mmol), N,N-methylbenzaylamine (0.12 mL, 0.99 mmol), chlorobenzene (0.15 mL, 1.47 mmol) and toluene (3 mL) were added to the schlenk. The mixture was heated to 105° C. for 24 h. GC-MS analysis indicated complete conversion of N,N-methylbenzylamine. The desired carboxamide product was formed in 76% yield.

Example 5:

A Schlenk tube containing $K_3PO_4$ (424 mg, 2.0 mmol) was degassed thoroughly under vacuum and refilled with argon. Benzaldehyde (0.20 mL, 1.97 mmol), N,N-methylbenzaylamine (0.12 mL, 0.99 mmol), chlorobenzene (0.15 mL, 1.47 mmol) and toluene (2 mL) were added to the schlenk followed by the addition of a toluene solution of catalyst (1.0 mL, containing $Pd(OAc)_2$ (1.0 mg, 4.5 μmol) and ligand A (5.0 mg, 14 μmol). The mixture was heated to 105° C. for 24 h. GC-MS analysis indicated complete conversion of N,N-methylbenzylamine. The desired carboxamide product was formed in 97% yield.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. Synthesis of a carboxamide from an aldehyde and an amine comprising, reacting said aldehyde and amine in the presence of oxidant, base and either a metal-ligand complex or ligand and metal precursor composition.

2. The reaction of claim 1, wherein said aldehyde is characterized by the general formula: $R^1CHO$, where $R^1$ is selected from the group consisting of hydrocarbyl, substituted hydrocarbyl, heteroatom-containing hydrocarbyl, and substituted heteroatom-containing hydrocarbyl.

3. The reaction of claim 1, wherein said amine is characterized by the general formula: $R^2R^3NH$, where each of $R^2$ and $R^3$ is independently selected from the group consisting of hydrocarbyl, substituted hydrocarbyl, heteroatom-containing hydrocarbyl, and substituted heteroatom-containing hydrocarbyl, and optionally either $R^2$ or $R^3$ is hydrogen, and optionally, $R^2$ and $R^3$ are joined together in a ring structure having between 3 and 50 non-hydrogen atoms in said ring.

4. The reaction of claim 1, wherein said carboxamide is characterized by the general formula:

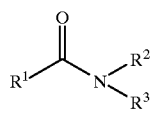

where $R^1$ is selected from the group consisting of hydrocarbyl, substituted hydrocarbyl, heteroatom-containing hydrocarbyl, and substituted heteroatom-containing hydrocarbyl; and $R^2$ and $R^3$ is independently selected from the group consisting of hydrocarbyl, substituted hydrocarbyl, heteroatom-containing hydrocarbyl, and substituted heteroatom-containing hydrocarbyl, and optionally either $R^2$ or $R^3$ is hydrogen, and optionally, $R^2$ and $R^3$ are joined together in a ring structure having between 3 and 50 non-hydrogen atoms in said ring.

5. The reaction of claim 1, wherein said ligand is selected from the group consisting of $PR_3$, $NR_3$, $OR_2$ or $:CR_2$ wherein each R is independently selected from the group consisting of hydrocarbyl, substituted hydrocarbyl, heteroatom-containing hydrocarbyl and substituted heteroatom-containing hydrocarbyl.

6. The reaction of claim 5, wherein each R is independently selected from the group consisting of alkyl, substituted alkyl, aryl, substituted aryl and combinations thereof.

7. The reaction of claim 1, wherein said oxidant is aryl halide is characterized by the general formula:

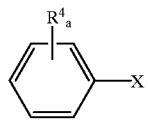

where $R^4$ is selected from the group consisting of hydrido, hydrocarbyl, substituted hydrocarbyl, heteroatom-containing hydrocarbyl, substituted heteroatom-containing hydrocarbyl, silyl, boryl, phosphino, amino, thio, seleno, and combinations thereof and a is 0, 1, 2, 3, 4 or 5; and optionally two or more $R^4$ groups are joined together in a ring structure.

8. The reaction of claim 7, wherein a is 0 and X is Cl.

9. The reaction of claim 1, wherein said ligand that is characterized by the general formula:

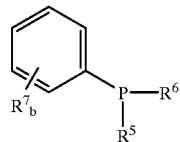

wherein each $R^5$ and $R^6$ is independently selected from the group consisting of alkyl and substituted alkyl; and $R^7$ is selected from the group consisting of hydrido, hydrocarbyl, substituted hydrocarbyl, heteroatom-containing hydrocarbyl and substituted heteroatom-containing hydrocarbyl, silyl, boryl, phosphino, amino, thio, seleno, and combinations thereof; and b is 0, 1, 2, 3, 4 or 5; and optionally two or more $R^7$ groups are joined together in a ring structure.

10. The reaction of claim 9, wherein each $R^5$ and $R^6$ is cyclohexyl or tert-butyl.

11. The reaction of claim 1, wherein said metal is in the form of a metal precursor that is characterized by the formula $M(L)_n$ where M is a metal selected from the group consisting of Groups 5, 6, 7, 8, 9 and 10 of the Periodic Table of Elements; L is an anionic or neutral compound and n is an integer greater than 0.

12. The reaction of claim 11, wherein M is selected from the group consisting of Ni, Pd, Fe, Pt, Ru, Rh, Ir and Co.

13. The reaction of claim 12, wherein M is selected from the group consisting of Ni or Pd.

14. The reaction of claim 11, wherein L is selected from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof.

15. The reaction of claim 1, wherein said aldehyde is generated from the oxidation of an alcohol substrate in a one-pot synthesis.

16. The reaction of claim 1, further comprising a solvent in the reaction mixture.

17. A reaction characterized by the following scheme:

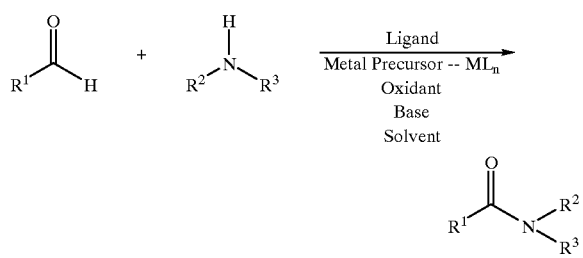

wherein:

$R^1$ is selected from the group consisting of hydrocarbyl, substituted hydrocarbyl, heteroatom-containing hydrocarbyl, and substituted heteroatom-containing hydrocarbyl each of $R^2$ and $R^3$ is independently selected from the group consisting of hydrocarbyl, substituted hydrocarbyl, heteroatom-containing hydrocarbyl, and substituted heteroatom-containing hydrocarbyl, and optionally either $R^2$ or $R^3$ is hydrogen, and optionally, $R^2$ and $R^3$ are joined together in a ring structure having between 3 and 50 non-hydrogen atoms in said ring;

Ligand is selected from the group consisting of $PR_3$, $NR_3$, $OR_2$ or $:CR_2$ wherein each R is independently selected from the group consisting of hydrocarbyl, substituted hydrocarbyl, heteroatom-containing hydrocarbyl and substituted heteroatom-containing hydrocarbyl;

$M(L)_n$ is where M is a metal selected from the group consisting of Groups 5, 6, 7, 8, 9 and 10 of the Periodic Table of Elements, L is an anionic or neutral compound and n is an integer greater than 0;

Oxidant is characterized by the general formula $R^4{}_a$—Ph—X where X is selected from the group consisting of Cl, Br, F and I, each $R^4$ is independently selected from the group consisting of hydrocarbyl, substituted hydrocarbyl, heteroatom-containing hydrocarbyl, substituted heteroatom-containing hydrocarbyl, silyl, boryl, phosphino, amino, thio, seleno and combinations thereof, and a is 0, 1, 2, 3, 4 or 5, and optionally two or more $R^4$ groups are joined together in a ring structure;

Base is selected from the group consisting of organic and inorganic bases; and

Solvent is selected from the group consisting of coordinating and non-coordinating solvents.

* * * * *